United States Patent
Wawro

[11] Patent Number: 6,095,983
[45] Date of Patent: Aug. 1, 2000

[54] ELECTRO-PNEUMATIC ASSEMBLY FOR BLOOD PRESSURE CUFF

[75] Inventor: Thaddeus J. Wawro, Auburn, N.Y.

[73] Assignee: Welch Allyn, Inc., Skaneateles Falls, N.Y.

[21] Appl. No.: 09/122,528

[22] Filed: Jul. 24, 1998

[51] Int. Cl.⁷ ................................................. A61N 5/00
[52] U.S. Cl. ................... 600/485; D24/186; 606/202
[58] Field of Search ................... 600/481–507, 600/300; 606/202; 128/897–899

[56] References Cited

U.S. PATENT DOCUMENTS

| | | |
|---|---|---|
| 3,405,707 | 10/1968 | Edwards . |
| 3,480,004 | 11/1969 | Edwards . |
| 3,896,791 | 7/1975 | Ono . |
| 4,290,434 | 9/1981 | Jewett . |
| 4,337,778 | 7/1982 | Akira et al. . |
| 4,890,625 | 1/1990 | Sorensen . |
| 5,092,338 | 3/1992 | Ide et al. . |
| 5,103,833 | 4/1992 | Apple . |
| 5,220,925 | 6/1993 | Hishida . |
| 5,335,665 | 8/1994 | Suzuki . |

*Primary Examiner*—Cary O'Connor
*Assistant Examiner*—Michael Astorino
*Attorney, Agent, or Firm*—Wall Marjama Bilinski & Burr

[57] ABSTRACT

A conduit assembly according to the invention includes a first member comprising a pair of integral conduit sections which interface with a custom connector having a first pair of distal connectors for receiving the receptacles of the duel lumen tube and a second pair of proximal connectors for receiving a shroud and an air tube, respectively. Received at the first proximal connector is a shroud for shielding electrical wiring. Received at the second proximal connector is a distal end of a pneumatic tube, which at its proximal end is connected to an air tube extending from an inflatable section of a cuff. The custom connector minimizes the area of and severity of seams and crevices at a separation area of electrical and pneumatic leads, and assures that the area of separation will endure only minimal mechanical degradation over the course of the device's use.

18 Claims, 3 Drawing Sheets

ELECTRO-PNEUMATIC ASSEMBLY FOR BLOOD PRESSURE CUFF

BACKGROUND OF THE INVENTION

1. Field of the Invention

The present invention relates to conduit structures for containing electrical wiring, and for providing a fluid channel, and particularly to a conduit assembly for incorporation in an automatic read type blood pressure reading device.

2. Background of the Prior Art

Automatic read blood pressure reading devices include generally a blood pressure cuff having an inflatable section and a microphone for generating electrical signals indicative of blood flow. These reading devices require therefore several types of input leads. In particular, they require electrical power wires for supplying voltage to the microphone, an electrical signal wire for carrying an electrical signal from a microphone, and an air tube for supplying air to an inflatable section of the cuff.

The multiple input leads of these devices create certain potential operational problems. One problem which has been noted with prior art automatic blood pressure measuring devices is that the multiple input leads have a tendency to get entangled during use. Another problem noted with automatic type blood pressure measuring devices is that electrical input leads of these devices in particular have been observed to become structurally weakened from stresses encountered during use. Still another problem with these devices is that prior art structures for containing multiple input leads typically have associated therewith seams and crevices which tend to trap contaminants and particalated matter, including blood. An example is the device described in U.S. Pat. No. 3,906,937 wherein particulate is readily trapped in crevices defined between a proximal end of a conduit housing which houses air tube and an insulated conductor, and the exterior surfaces of the tube and the conductor.

There is a need for an improved conduit assembly for an automatic blood pressure cuff.

SUMMARY OF THE INVENTION

According to its major aspects and broadly stated the present invention is a multipart electro-pneumatic conduit assembly for an automatic blood pressure measuring device of the type requiring both electrical leads and pneumatic leads.

A conduit assembly according to the invention includes a dual lumen tube which interfaces with a custom connector having a first pair of connectors for receiving the receptacles of the dual lumen tube and a second pair of connectors for receiving a shroud and an air tube, respectively.

Received at the first connector of the second pair of connectors of the custom connector is a shroud for shielding electrical wiring. Received at the second connector of the second pair of connectors is a distal end of a pneumatic tube, which at its proximal end is connected to an air tube extending from an inflatable section of a cuff. The custom connector minimizes the area of and severity of seams and crevices at a separation area of electrical and pneumatic leads, and assures that the of separation area will endure only minimal mechanical degradation over the course of a device's use.

In a preferred embodiment of the invention, the shroud is connected via an appropriate connector to a sectioned flexible sleeve extending from a microphone. The sectioned flexible sleeve limits the amount of bending of lead wires extending from a microphone.

These and other details, advantages and benefits of the present invention will become apparent from the detailed description of the preferred embodiment hereinbelow.

BRIEF DESCRIPTION OF THE DRAWINGS

The preferred embodiment of the invention will now be described, by way of example only, with reference to the accompanying Figures wherein like members bear like reference numerals and wherein.

DETAILED DESCRIPTION OF THE PREFERRED EMBODIMENT

Figure 1:
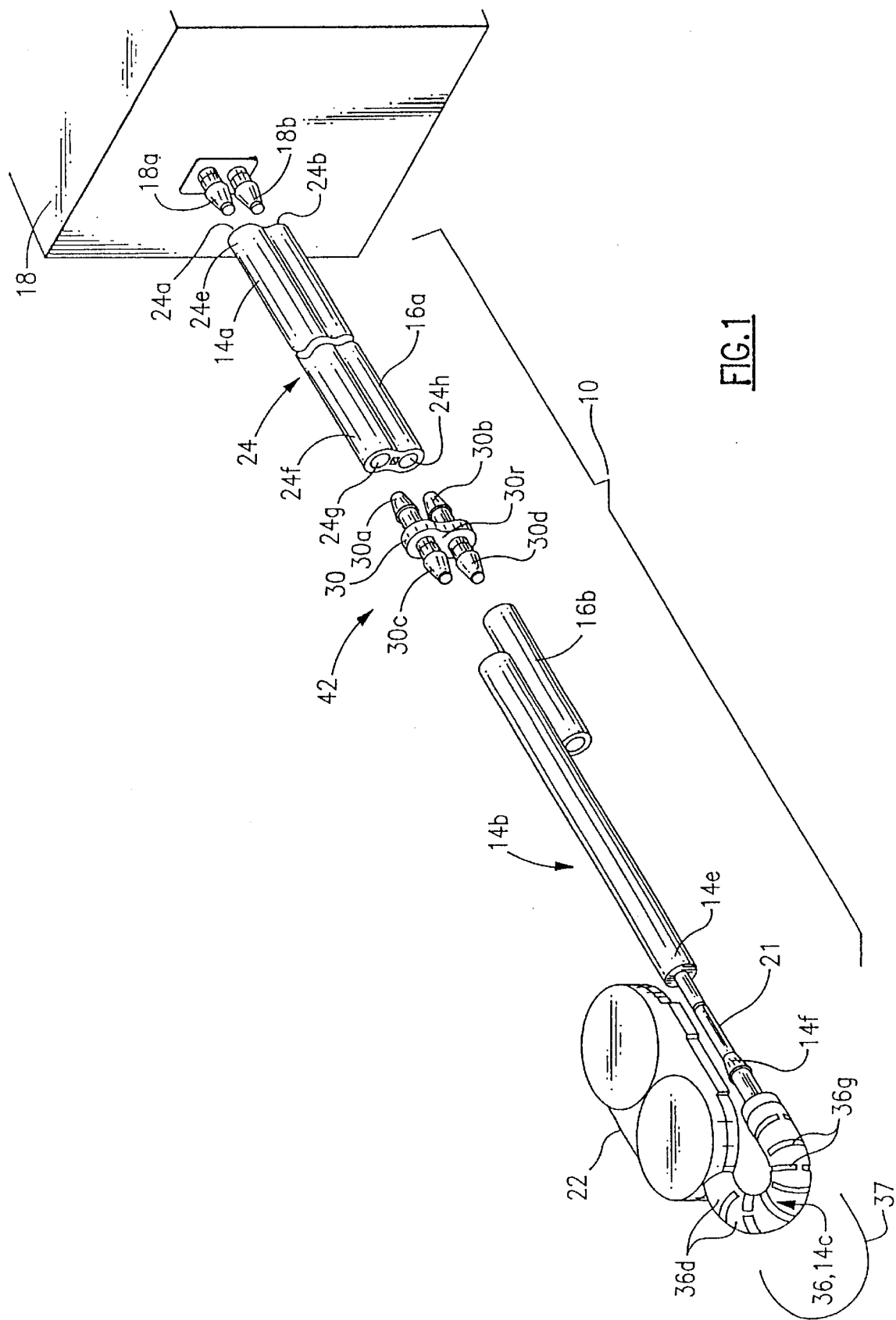
FIG. 1 is a perspective assembly diagram of a conduit assembly according to the invention.
Figure 2:
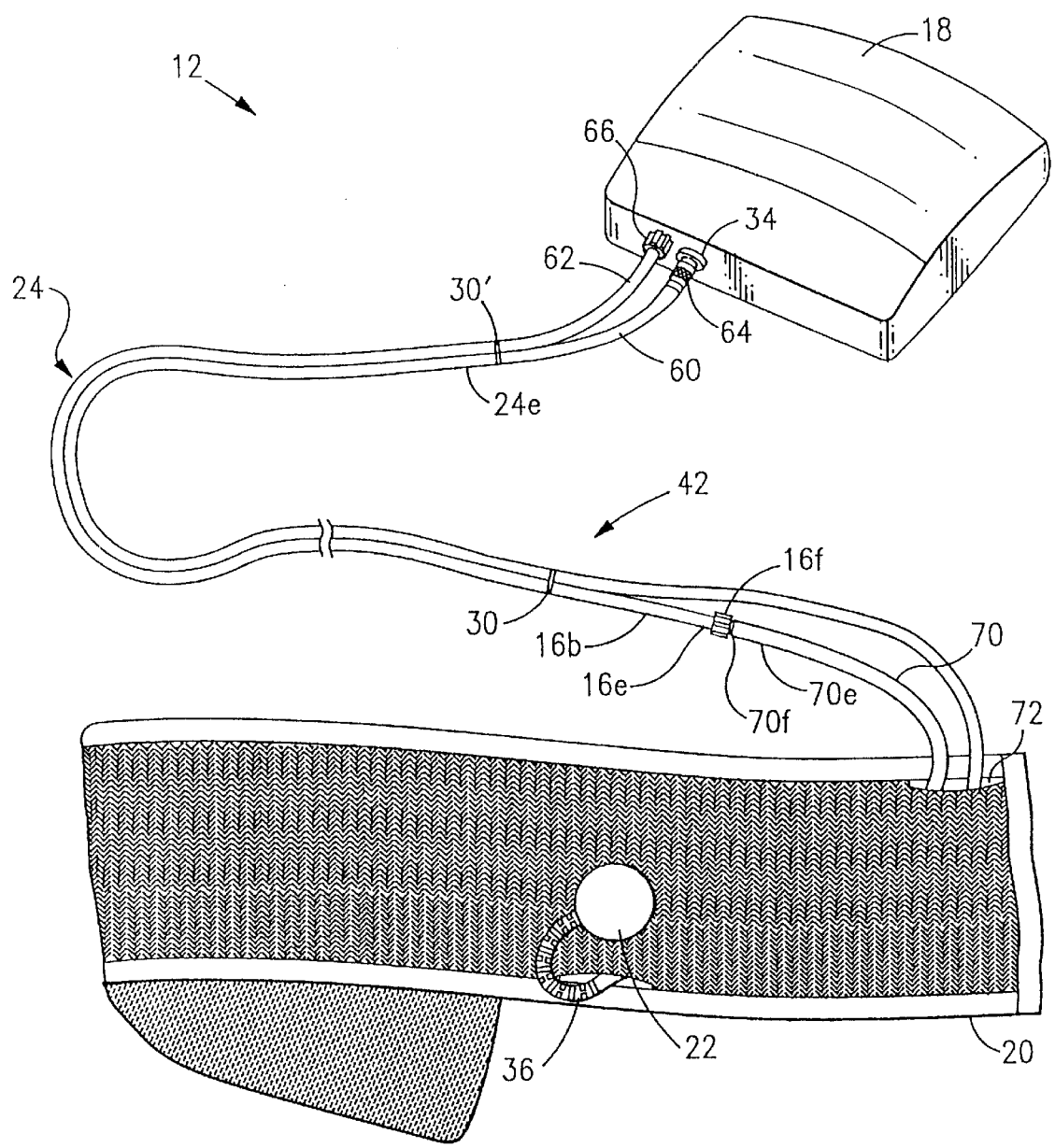
FIG. 2 is a perspective diagram of a blood pressure reading device in which a conduit assembly according to the invention is incorporated.

The invention is described with reference to FIG. 1 showing an assembly detail of a conduit assembly 10 according to the invention, and FIG. 2 showing the conduit assembly incorporated into a blood pressure cuff reading device 12. Conduit assembly 10 for automatic blood pressure reading device 12 includes an electrical conduit comprising sections 14a and 14b and a fluid conduit comprising sections 16a and 16b, for carrying electrical wiring 21 and air, respectively, from electrical/air supply and control unit 18 (hereinafter, control unit) to blood pressure cuff 20. Control unit 18 includes an electrical power supply for supplying voltage to a blood flow sensing device such as a microphone 22, an air supply unit and associated motor, and processing circuitry for receiving an electrical signal generated by microphone 22, and for calculating therefrom a reading of blood pressure. Referring now to particular aspects of conduit assembly 10, assembly 10 comprises a first member 24 comprising two connected conduit sections 14a and 16a. The sections 14a and 16a are connected such that the two sections share a substantially smooth integrated outer surface as is shown. First member 24 having the described characteristics can be termed a "dual lumen tube". Shown in FIG. 1 as having a "figure eight" cross-section, the dual lumen tube can be made to have virtually any cross-section including circular elliptical, rectangular, star shaped, etc. Dual lumen tube 24 may comprise a durable flexible material such as thermoplastic elastomer and may be made by a process of extrusion molding.

In the example provided, receptacles 24a and 24b defined at distal end 24e of first member 24 are adapted to be fitted onto male connector ends 18a and 18b of control unit 18. Receptacles 24a and 24b, like all receptacles described herein can optionally be permanently bonded to their associated connectors with use of a suitable bonder material. One preferred bonder material is LOCTITE of the type sold by Loctite Corp. of Hartford, Conn.

Receptacles 24g and 24h defined at proximal end 24f of dual lumen tube 24, meanwhile, are received in distal male connector end 30a and 30b of a custom connector 30 comprising a pair of distal male connectors, and oppositely directed proximal male connectors. Custom connector 30 could also be provided with female connectors or a combination of male/female connectors.

Received in proximal male connector ends 30c and 30d of custom connector 30 are shroud 14b and pneumatic tube 16b. Shroud 14b along with first conduit section 14a of dual lumen tube 24 form the major part of containment for insulated electrical wiring connecting unit 18 and microphone 22 while pneumatic tube 16b and second conduit section 16a of dual lumen tube 24 form the major part of the air channel guiding air supplied by unit 18 to cuff 20.

As best seen in FIG. 2, distal end 16e of pneumatic tube 16b terminates in female fitting 16f which is received in male end fitting 70f at a distal end 70e of an air tube 70 emanating from cuff 20 which is in fluid communication with an inflatable section of cuff 20. Fittings 16f and 70f are adapted to be manually removable such that the fittings can be connected by friction forces in a seal tight arrangement without the aid of adhesives or bonding material, and disconnected via manually pulling the fittings apart.

Distal end 14e of shroud 14b, meanwhile, is received by male connector 14f at a distal end of sectioned flexible sleeve fitting 36, 14c. Connector 14f may be secured to or formed integral with sectioned sleeve 36. Sectioned flexible sleeve 36 is of the type comprising disc sections 36d separated by gap sections 36g which allow flexing of the sleeve 36. Preferably, sectioned sleeve fitting 36 is secured to or formed integral with the casing of microphone 22. In one embodiment of the invention shroud 14b may be deleted and sectioned sleeve 36 may be adapted to be connected directly to custom fitting 30.

Figure 3A:
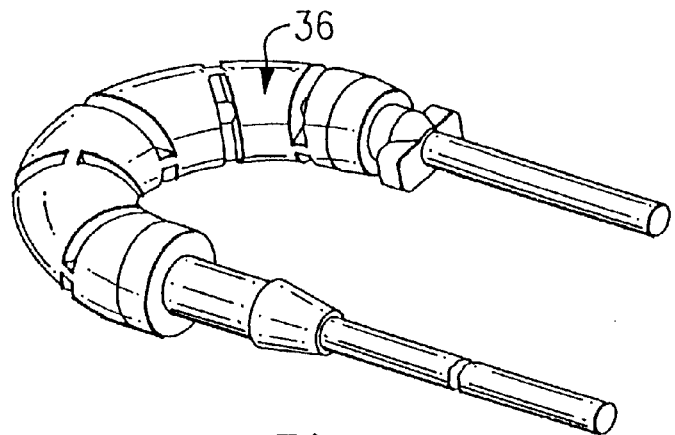
FIGS. 3a and 3b show examples of possible alternative embodiments of a sectioned sleeve described herein.
Figure 3B:
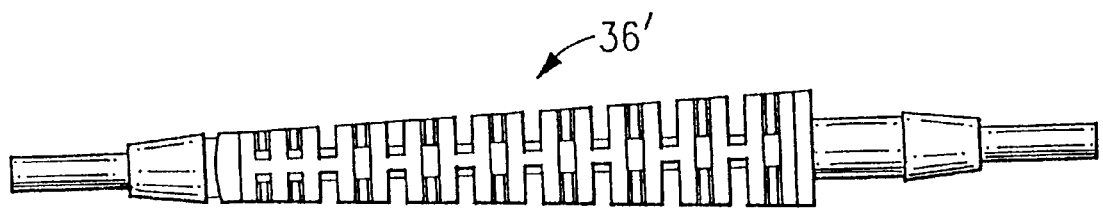

Examples of alternative embodiments for sectioned sleeve 36 are shown in FIGS. 3a and 3b. In the example of FIG. 3a, sectioned sleeve 36 is formed in a normally curved configuration. In the example of FIG. 3b, meanwhile, section sleeve 36 is tapered toward its proximal end to enable pronounced bending of sleeve toward a proximal end of the sleeve. Sectioned sleeve 36 typically comprises a thermoplastic elastomer and is typically formed by an injection molding process.

It will be seen that the above conduit assembly has certain operational advantages over prior art conduit assemblies for automatic blood pressure reading devices. Dual lumen tube 24 having smooth outer surface provides two major advantages. First, dual lumen tube 24 maintains the electrical leads and pneumatic leads in closed space relation, and thereby reduces the possibly that the leads will become entangled. Second, the smooth outer surface of dual lumen tube 24 does not readily trap particulate, is easily cleaned and therefor is advantageous from a hygiene standpoint.

Custom fitting 30 having two pairs of oppositely directed connectors further reduces the number of crevice and seam particulate-trapping area as compared to prior art devices. In the case that a conduit is disposed about electrical pneumatic leads, as is the case with the device shown in U.S. Pat. No. 3,906,937 there are formed particulate trapping seams and crevices at the Y where the electrical and pneumatic leads extend from the end of a conduit and separate. The seams and crevices in the design of the '937 patent become more pronounced over the course of repeated use as stresses are imparted on the leads.

The conduit assembly of the present invention provides a separation area 42 between an electrical lead 14b and a pneumatic lead 16b that greatly reduces the size and severity of particulate trapping crevices and seams as compared to the design shown in U.S. Pat. No. 3,906,937. In the design of FIG. 2 separation point seams and crevices consist only of the small seams between a tube (or shroud) and custom connector 30. The widths of these seems can be reduced by tightly pushing a tube or shroud against a retainer 30r of custom connector member 30 and/or by connecting a tube or shroud to a connector 30 with use of a bonding material. Furthermore, it will be seen that particulate that does enter through a seam cannot penetrate deeply into a contained are as is the case with the design shown in U.S. Pat. No. 3,906,937.

Still further, it can be seen that custom connector 30 enhances the overall structural integrity of conduit assembly 10. Stresses can be applied to the leads 14b and 16b over time during use of a device without significant alteration of the mechanical properties of the conduit assembly at the area 42 of lead separation.

The advantages derived by providing custom fitting 30 can be improved further by specially configuring retainer 30r of custom fitting 30. If a cross section of retainer 30r is formed to be similar or essentially the same as the cross-section of dual lumen tube 24, as is shown in FIGS. 1 and 2, then the severity of seams and crevices in the area about connector 30 is further reduced.

A retainer cross-section that is formed complementary with the cross-section of dual lumen tube 24 can be, for example, figure eight shaped as shown, circular, elliptical, rectangular, or star shaped, etc.

Figure 4:
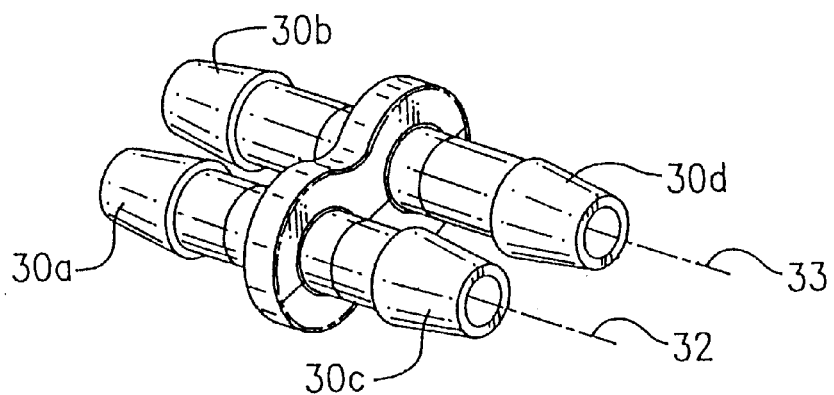
FIG. 4 is a perspective view of an enhanced version of a custom connector described herein.

The operational characteristics of custom connector 30 can be enhanced still further by configuring the connector in accordance with the design of FIG. 4. In the design of FIG. 4 first distal and first proximal connectors 30a and 30c which are adapted to contain electrical wiring are sized to lengths shorter than the lengths of second distal 30b and second proximal connector 30d. It can be seen that this configuration prevents certain structural stresses from being imparted on electrical wiring 21 of the conduit assembly. In particular, the arrangement characterized by the ends of second distal and proximal connectors rigidly extending beyond the ends of first proximal and distal connectors prevents tube section 14a and shroud 14b from being radically bent at a near right angle about fitting 30 along a plane that runs through the axes 32 and 33 of the first and second connector sections. Thereby, the arrangement prevents stresses from being imparted on wiring 21 which might otherwise result from radical bending of shroud 14b or tube section 14a about fitting 30.

Other advantages of conduit assembly 10 are provided by the design of sectioned sleeve fitting 36 extending from microphone 22. The first few inches of electrical lead wire extending from microphone 22 encounter more stresses during use than perhaps any other length of pneumatic or electrical lead in device 12. In use, as is illustrated in FIG. 2, microphone 22 is fitted through slot 72 of cuff 20, and lead 16 is folded to form an elbow just before the point where microphone is attached, so the microphone contacts skin of a patient while being biased toward skin by cuff 20. The arrangement provides good retention of the microphone within cuff 20, while allowing microphone 22 to be easily adjusted to a point where it can optimally generate electrical signals indicative of blood flow. However, it can be seen that the arrangement requires the electrical wiring near microphone 22 encounter significant stresses resulting from the wires being repeatedly bended and straightened.

Sectioned flexible sleeve 36 allows electrical lead wires near microphone 22 to endure such stresses. While sectioned flexible sleeve 36 protects lead wires from stresses applied by many different sources, the primary function of sectioned sleeve 36 is to limit the severity of bending of the lead wires. Without sectioned sleeve 36 it can be seen that wires could be bent severely, even creased, during folding of microphone 22 into good reading position. Sectioned sleeve 36 forces lead wires to be bended along a gradual arc as indicated arc 37 by FIG. 1 when microphone 22 is folded into a position facilitating good reading.

It is seen that unit 18 of FIG. 2 includes a specially adapted electrical plug 54 and an air tube fitting receptacle (hidden from view). If unit 18 is so equipped, conduit assembly 10 can be readily adapted for use in such a unit. A second custom fitting 30 comprising two pairs of connectors can be fitted to distal end 24e of tube 24 and additional leads 60 and 62 which terminate in an electrical plug receptacle 64 and an tube plug receptacle 66 can be connected to connectors at the distal end of second custom fitting 30.

While the present invention has been particularly shown and described with reference to the preferred mode as illustrated in the drawing, it will be understood by one skilled in the art that various changes in detail may be effected therein without departing from the spirit and scope of the invention as defined by the claims.

What is claimed is:

1. A conduit assembly for a blood pressure reading device of the type including a blood flow sensing device and a cuff having an inflatable section, said conduit assembly comprising:

a first member including a pair of integrated conduit sections sharing a common outer surface, said first member having a distal end and a proximal end; and a custom fitting comprising a first and second distal connectors and first and second proximal connectors, said custom connector being connected to said first member.

2. The assembly of claim 1, further comprising a shroud connected to said first proximal connector.

3. The assembly of claim 1, further comprising a pneumatic tube connected to said second proximal connector.

4. The assembly of claim 1, further comprising a sectioned sleeve connected to said first proximal connector.

5. The assembly of claim 4, wherein said sectioned sleeve comprises disc sections separated by gap sections.

6. The assembly of claim 2, further comprising a sectioned sleeve connected to said shroud.

7. The assembly of claim 4, wherein said sectioned sleeve is attached on one end to said blood flow sensing device.

8. The assembly of claim 6, wherein said sectioned sleeve is attached on one end to said blood flow sensing device.

9. The assembly of claim 1, wherein said custom fitting includes a retainer, said retainer having a cross-section corresponding to a cross-section of said first member.

10. The assembly of claim 1, wherein said first and second proximal connectors are male-ended, and wherein said first proximal connector is sized to a different length than said second proximal connector.

11. The assembly of claim 1, wherein said first and second distal connectors are male-ended, and wherein said first distal connector is sized to a different length than said second proximal connector.

12. The assembly of claim 3, wherein said pneumatic tube is connected at one end to an air tube extending from a cuff inflatable section.

13. A conduit assembly for a blood pressure reading device of the type including a blood flow sensing device, at least one electrical conductor extending from said device, and a cuff including an inflatable section, said conduit assembly comprising a sectioned sleeve extending from said blood flow sensing device, said sectioned sleeve housing said at least one electrical conductor to limit bending of said at least one electrical conductor.

14. The conduit assembly of claim 13, wherein said sectioned sleeve includes disc sections separated by gap sections.

15. The conduit assembly of claim 13, wherein said section sleeve contains electrical wiring, and wherein said sectioned sleeve is configured to limit bending of said electrical wiring.

16. The conduit assembly of claim 13, wherein said sectioned sleeve is of a normally curved configuration.

17. The conduit assembly of claim 13, wherein said sectioned sleeve is tapered toward its proximal end.

18. The conduit assembly of claim 13, further comprising a male end connector integrally formed at a distal end of said sectioned sleeve.

* * * * *